United States Patent [19]
Weister

[11] Patent Number: 5,915,825
[45] Date of Patent: Jun. 29, 1999

[54] ILLUMINATED MIRROR TOOL

[76] Inventor: Kenneth Weister, 317 Georgetown Rd., Beaver Falls, Pa. 15010

[21] Appl. No.: 09/074,917

[22] Filed: May 8, 1998

Related U.S. Application Data

[60] Provisional application No. 60/045,865, May 8, 1997.

[51] Int. Cl.[6] .................................................. F21V 33/00
[52] U.S. Cl. ........................... 362/139; 362/138; 362/191
[58] Field of Search .................................... 362/135, 138, 362/139, 142, 191, 208, 197

[56] References Cited

U.S. PATENT DOCUMENTS

| | | |
|---|---|---|
| D. 341,220 | 11/1993 | Eagan ........................................ D26/43 |
| 2,652,479 | 9/1953 | Wilson ...................................... 362/138 |
| 4,212,105 | 7/1980 | Hukuba ..................................... 433/30 |
| 4,629,425 | 12/1986 | Detsch ...................................... 433/31 |
| 5,139,421 | 8/1992 | Verderber ................................. 433/31 |
| 5,348,470 | 9/1994 | McGowan et al. ...................... 433/30 |
| 5,428,484 | 6/1995 | Baker ....................................... 359/872 |
| 5,636,918 | 6/1997 | Lott ......................................... 362/139 |

*Primary Examiner*—Stephen Husar

[57] ABSTRACT

A holder has a first aperture and a second aperture adapted to receive a light source and a wand of a mirror assembly, respectively. The holder positions the light source and the mirror assembly so that light from the light source is received by a mirror of the mirror assembly. Suitable manipulation of the holder enables the mirror assembly to be positioned so that a user can indirectly visualize an object in the presence of light from the light source reflected off the mirror.

20 Claims, 5 Drawing Sheets

5,915,825

ILLUMINATED MIRROR TOOL

This application claims the benefit of U.S. Provisional Pat. App. Ser. No. 60/045,865 filed May 8, 1997 entitled "Illuminated Mirror Tool"

BACKGROUND OF THE INVENTION

1. Field of the Invention

The present invention relates to an illuminated mirror tool useful for indirect visual inspection of hard to reach portions of objects, human subjects and animals.

2. Description of the Prior Art

Light sources such as flashlights are often utilized with hand-held telescoping mirrors to illuminate and visualize hard to reach areas of mechanical assemblies, humans subjects and animals. Such areas of mechanical assemblies include soldered joints of plumbing, remote and/or hard to reach portions of an automotive engine and heat exchangers of furnaces. Such areas of human subjects and animals include the teeth, the mouth and the throat. A problem with utilizing a hand-held light source is that it is often difficult to position the light source to project light on the portion of the object to be observed. Moreover, it is often difficult to both see and illuminate the object through a hand-held telescoping mirror simultaneously because the object is best illuminated by placing the light source directly in the line of sight which blocks one's view. Furthermore, an operator or user utilizing a light source in one hand and a mirror in the other hand has no available hands to work on the portion of the assembly, human subject or animal being viewed.

It is an object of the present invention to provide an illuminated mirror tool having a removably supported light source and mirror assembly.

It is also an object of the present invention to provide an illuminated mirror tool having an integrally formed light source and/or mirror assembly.

Still further objects of the invention will become apparent to those of ordinary skill in the art upon reading and understanding the ensuing detailed description.

SUMMARY OF THE INVENTION

The above objects are satisfied with an illuminated mirror tool of my invention which includes a holder having a first end and a second end. The holder can have a first aperture extending from the first end to the second end and a second aperture extending from the first end towards the second end. The illuminated mirror tool can also include a light source and a mirror assembly having a mirror connected to a wand. The first aperture is preferably adapted to receive the light source and the second aperture is preferably adapted to receive the wand of the mirror assembly. The holder can removably secure the mirror assembly and the light source so that light from the light source is receivable on the mirror of the mirror assembly.

The illuminated mirror tool may include a compressible material received in the first aperture and the second aperture. The compressible material can be positioned between the inner wall of the first aperture and the light source and can be adapted to provide a frictional interaction between the light source and the compressible material and between the compressible material and the inner wall of the first aperture, so that the light source can be removably secured in the first aperture. The illuminated mirror tool can also include the compressible material received in the second aperture, which can be positioned between the inner wall of the second aperture and the wand of the mirror assembly. The compressible material received in the second aperture can be adapted to provide a frictional interaction between the wand of the mirror assembly and between the compressible material and the inner wall of the second aperture, so that the wand of the mirror assembly can be removable secured in the first aperture.

The mirror assembly may include a universal joint located between the mirror and the wand, which can be adapted to enable the mirror to rotate around a longitudinal axis of the wand and to pivot about an axis transverse to the longitudinal axis of the wand. Further, the light source may include an on/off switch and the holder can be adapted so that the on/off switch projects through the holder. Additionally, the holder can include an on/off switch which by proper rotational and longitudinal alignment of the light source in the first aperture, the on/off switch of the light source can be aligned with the on/off switch of the holder so that the on/off switch of the light source can be engaged by the on/off switch of the holder. Finally, the light source can include a swivelable joint which can be adapted to enable the light source to emit light in directions other than parallel to the longitudinal axis of the light source.

In a second embodiment of the present invention, the mirror assembly can include a magnet located on the end of the wand opposite the mirror and the holder can include a piece of magnetic material positioned at the base of the second aperture. The magnet and the magnetic material can cooperate to magnetically secure the wand in the second aperture so that the wand is removably secured in the second aperture.

In a third embodiment of the present invention, the light source and/or the mirror assembly can be formed as an integral part of the holder. In another embodiment of the present invention, the compressible material may be replaced with a plurality of resilient projections. In still another embodiment of the present invention, a belt carrier can be utilized to transport the illuminated mirror tool.

These and other advantages of the present invention will be clarified in the description of the preferred embodiments taken together with the attached figures wherein like numerals represent like elements throughout.

DETAILED DESCRIPTION OF THE PREFERRED EMBODIMENTS

Figures 1, 2:
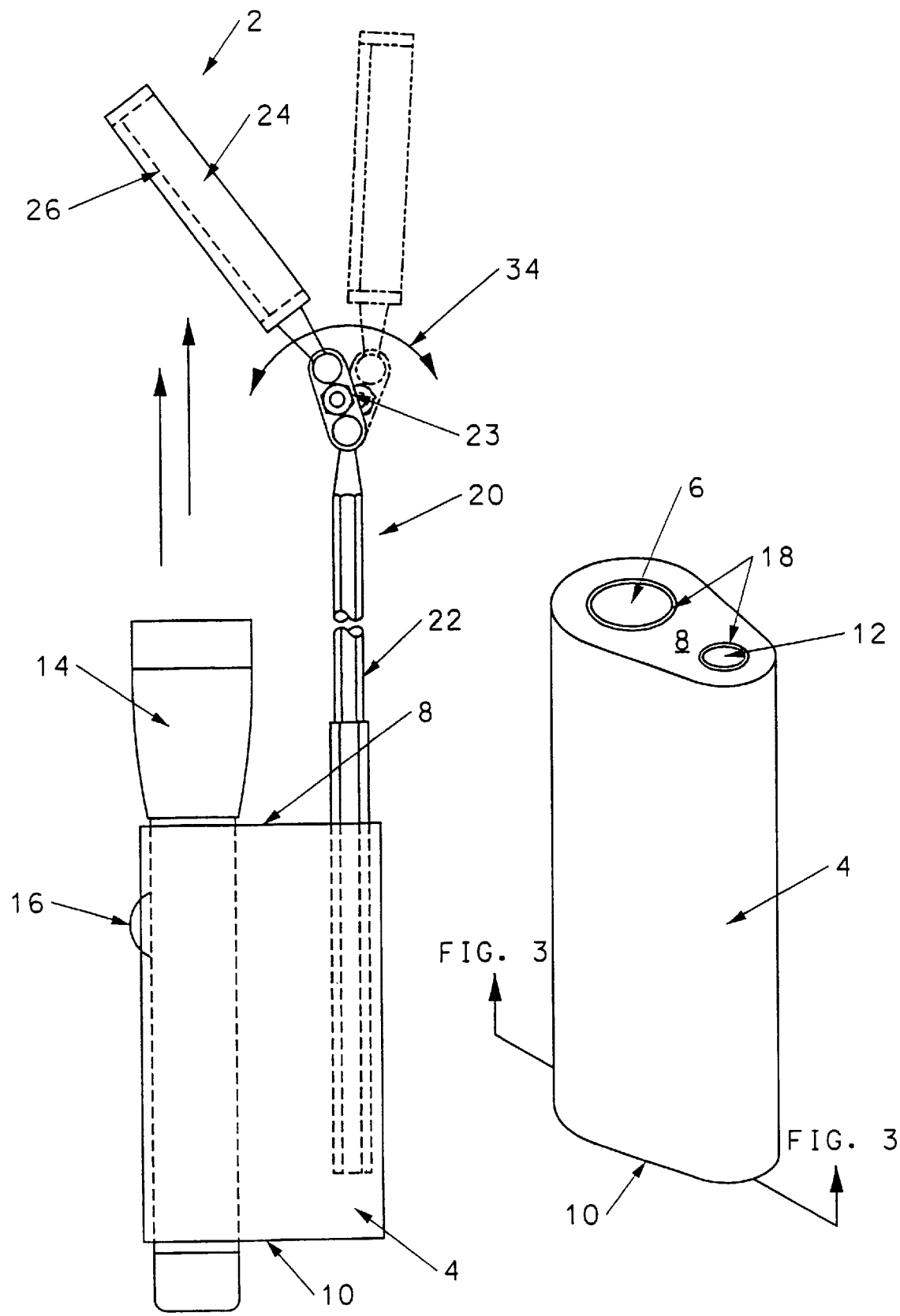
FIG. 1 is an side view of a first embodiment of the illuminated mirror tool of the present invention.
FIG. 2 is a perspective view of a holder of the illuminated mirror tool of FIG. 1.
Figure 4:
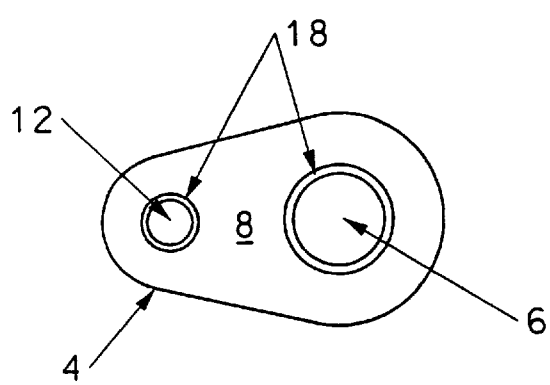
FIG. 4 is a top end view of the holder of the illuminated mirror tool of FIG. 2.
Figure 3:
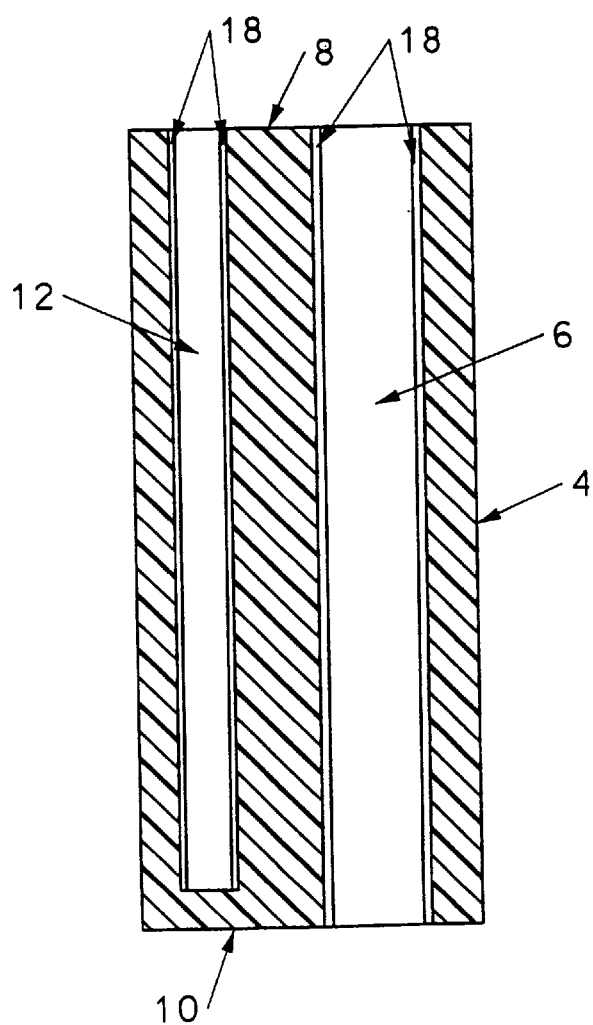
FIG. 3 is a sectional view of the holder of the illuminated mirror tool of FIG. 2 taken along line 3—3.

With reference to FIGS. 1–4, an illuminated mirror tool 2 includes a holder 4, preferably, having a generally oval shape. The holder 4 has a first aperture 6 formed therein between a first end 8 and a second end 10 of the holder 4. Alternatively, the first aperture 6 can terminate between the first end 8 and the second end 10.

The holder 4 also includes a second aperture 12 formed therein that extends from the first end 8 of the holder 4 towards the second end 10 thereof and preferably terminates therebetween. The holder 4 is formed of a rigid material such as aluminum or plastic.

Figures 9, 10, 11:
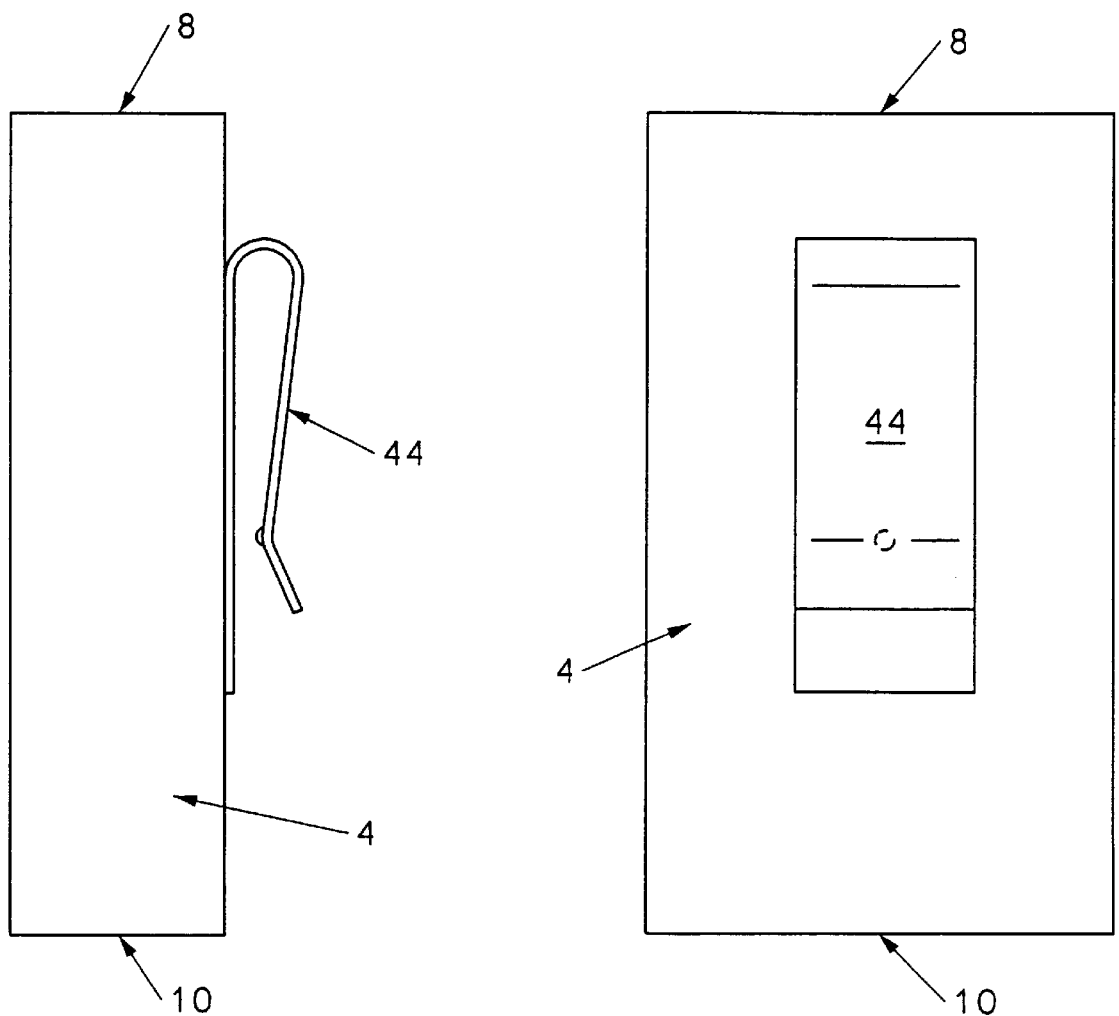
FIG. 9 is a top end view of a holder of a fourth embodiment of an illuminated mirror tool of the present invention showing a plurality of resilient projections in the apertures in the holder.
FIG. 10 is a side view of a holder of a fifth embodiment of an illuminated mirror tool of the present invention showing a belt carrier attached to the holder.
FIG. 11 is a rear view of the holder of FIG. 10.

The first aperture 6 is adapted to receive a conventional light source 14 therein, for example, a flashlight. The light source 14 includes an on/off switch 16. Positionable between the outer wall of the light source 14 and the inner wall of the first aperture 6 is a compressible material 18, such as foam rubber. The compressible material 18 is compressed between the outer wall of the light source 14 and the inner wall of the first aperture 6 thereby creating a frictional interaction between the outer wall of the light source 14 and the compressible material 18 and between the compressible material 18 and the inner wall of the first aperture 6. This frictional interaction enables the light source 14 to be firmly and removably secured in the first aperture 6. In the preferred embodiment the compressible material 18 is foam rubber, however, any material capable of providing the frictional interaction between the outer wall of the light source 14 and the compressible material 18 and between the compressible material 18 and the inner wall of the first aperture can be utilized in place of foam rubber. Further, the compressible material 18 can be formed as a plurality of resilient projections 19 adapted to removably secure the light source 14 in the first aperture 6, as shown in FIG. 9 and discussed later. The compressible material 18 may also be glued to the first aperture 6.

A mirror assembly 20 is removably secured in the second aperture 12. Specifically, the mirror assembly 20 includes a telescoping wand 22, a mirror 24 with a reflective face 26, and a universal joint 28 located between the telescoping wand 22 and mirror 24. The second aperture 12 is adapted to receive an end of the telescoping wand 22 opposite the universal joint 28. Positioned between the inner wall of the second aperture 12 and the telescoping wand 22 is compressible material 18. Frictional interaction between the telescoping wand 22 and the compressible material 18 and between the compressible material 18 and the inner wall of the second aperture 12 enables the mirror assembly 20 to be firmly and removably secured in the second aperture 12. Alternatively the compressible material 18 may be glued to the second aperture 12. The compressible material 18 located in the second aperture 12 can also be formed as the plurality of resilient projections 19 adapted to removably secure the telescoping wand 22 of the mirror assembly 20 in the second aperture 12, as shown in FIG. 9 and discussed later.

The compressible material 18 in the first aperture 6 and the second aperture 12 enable different diameters of light sources 14 and telescoping wands 22 to be utilized with holder 4, only being limited by the outer dimension of the first aperture 6 and the second aperture 12.

The holder 4 is preferably adapted so that the first aperture 6 enables the on/off switch 16 of the light source 14 to project through an opening in the holder 4 or otherwise be accessible from the extension of the holder 4.

Figure 5:
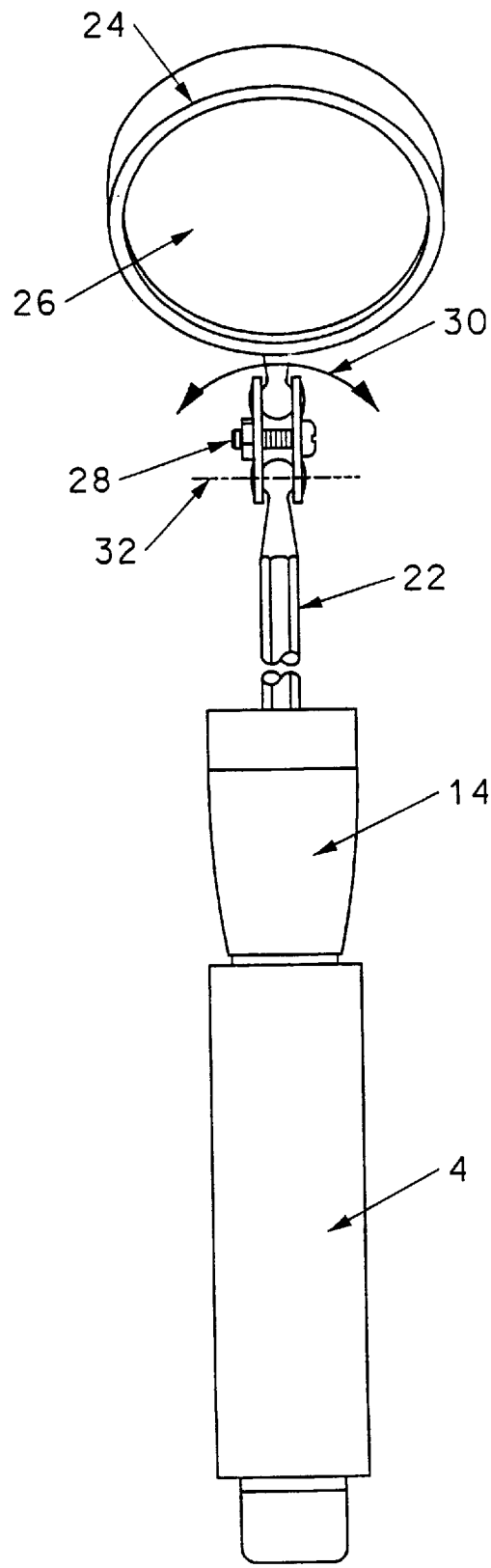
FIG. 5 is a front view of the illuminated mirror tool of FIG. 1.

With reference to FIG. 5 and with continued reference to FIG. 1, the universal joint 28 enables the mirror 24 to be rotated around the longitudinal axis of telescoping wand 22, as shown by arrows 30 in FIG. 5. The universal joint 28 also enables the mirror to be pivoted about an axis 32 that extends transverse, and preferably perpendicular, to the longitudinal axis of telescoping wand 22, as shown by arrows 34 in FIG. 1. The light source 14 and the mirror assembly 20 are positioned in the holder 4 so that light from the light source 14 is received by the reflective face 26 of the mirror 24. The telescoping wand 22 is extendable and retractable so that the mirror 24 can be moved away from and closer to the holder 4. The holder 4, and consequently the mirror 24 and light source 14, are positionable to enable indirect viewing of objects (not shown) via the mirror 24. Coincident with viewing the object, light from the light source 14 received on the reflective face 26 of the mirror 24 is reflected, thereby illuminating the portion of the object being indirectly viewed. Hence, the present invention enables simultaneous illumination and indirect viewing of an object, or a portion thereof, with one hand of a user.

The compressible material 18 in the first aperture 6 and the second aperture 12 enable the light source 14 and the mirror assembly 20 to be replaced. This is particularly advantageous when only one of the mirror assembly 20 and the light source 14 breaks. Hence, only the broken one of the light source 14 and mirror assembly 20 need be replaced, the unbroken one of the light source 14 and the mirror assembly 20 still being usable.

Figure 6:
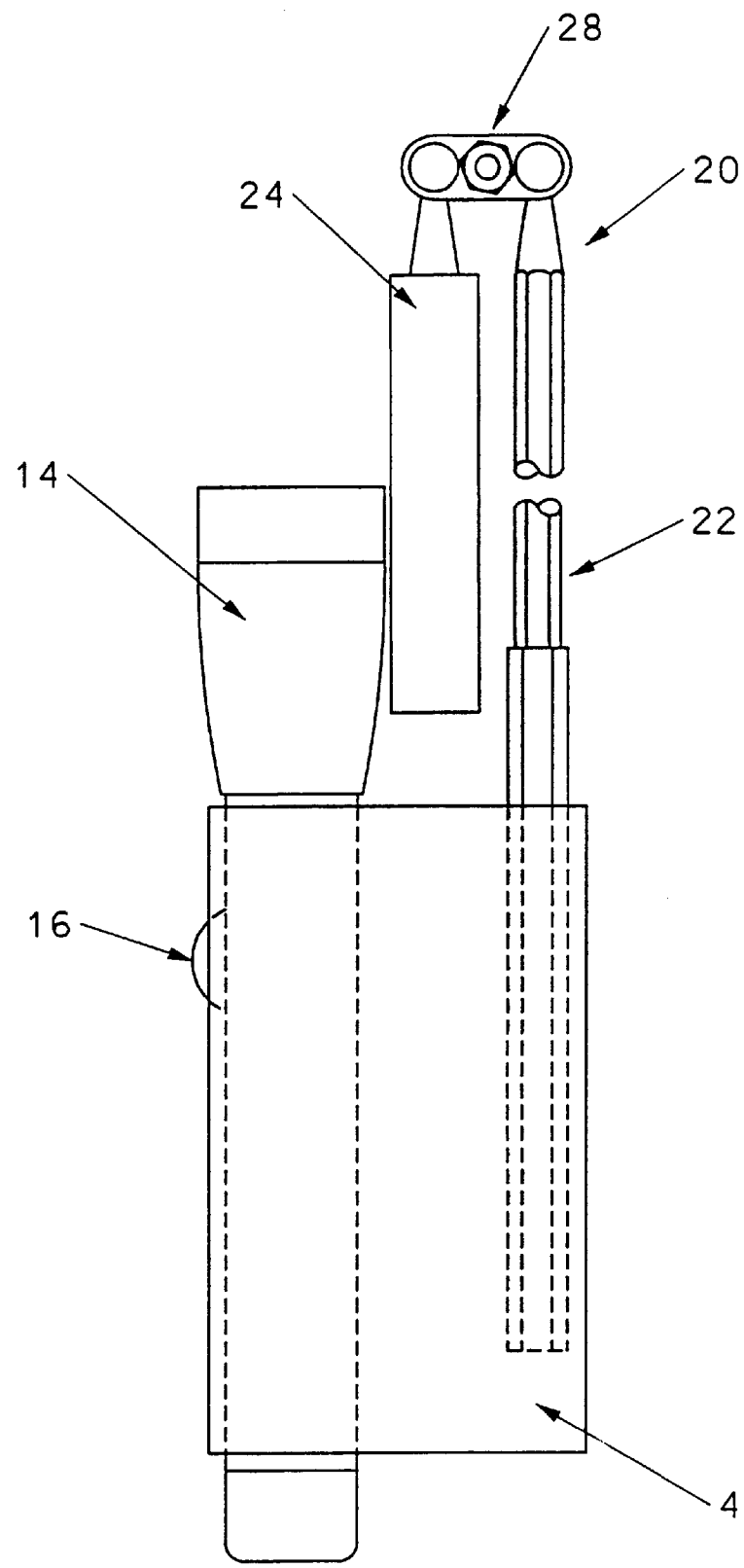
FIG. 6 is a side view of the illuminated mirror tool of FIG. 1 with the mirror in a retracted position.

With reference to FIG. 6, to enable the light source 14 to be utilized without utilizing the mirror 24, the universal joint 28 allows the mirror 24 to be folded adjacent the telescoping wand 22. The telescoping wand 22 is then retracted so that the mirror 24 is preferably positioned in a protective position between the light source 14 and the telescoping wand 22. Hence, the light source 14 is usable with the mirror 24 retracted adjacent holder 4. The protective position of the mirror 24 avoids contact with objects that may otherwise occur with the telescoping wand 22 extended.

Figure 7:
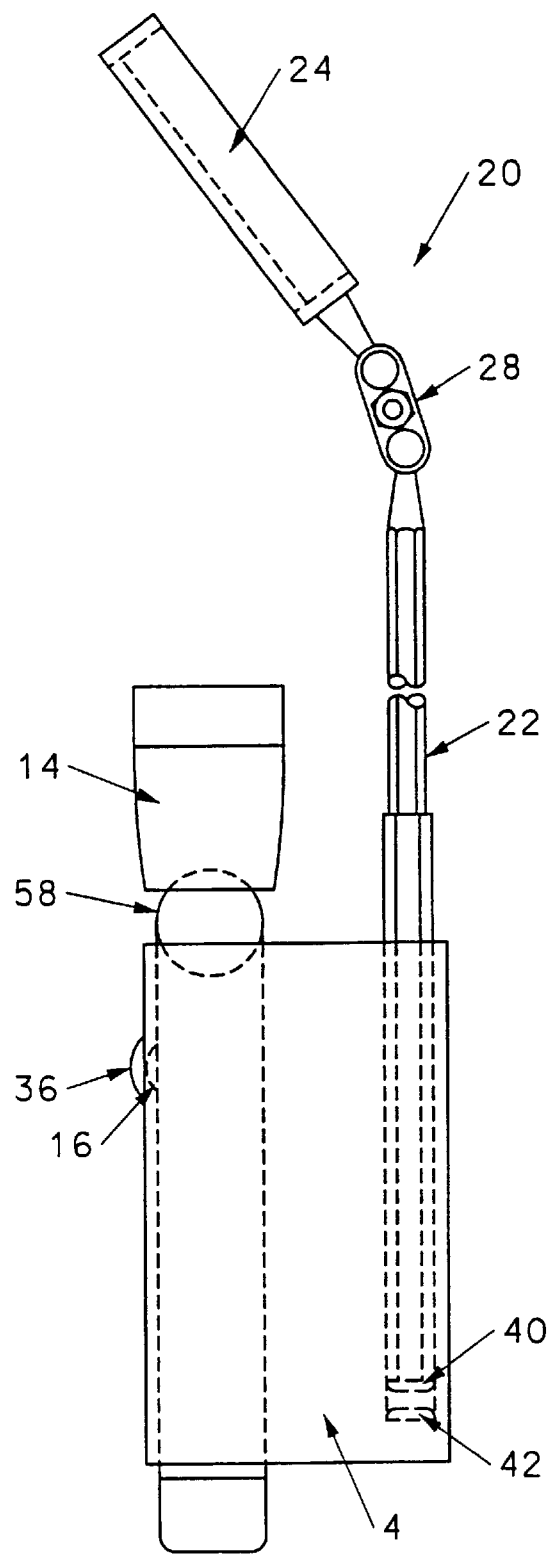
FIG. 7 is a side view of a second embodiment of an illuminated mirror tool of the present invention showing a light source with a swivelable head and a mirror assembly removably received within a holder of the illuminated mirror tool by a magnet.

With reference to FIG. 7, the holder 4 can include an on/off switch 36 adapted to cooperate with the on/off switch 16 of the light source 14. By appropriate positioning of the light source 14 in the first aperture 6, the on/off switch 16 of the light source 14 is aligned with the on/off switch 36 of the holder 4. Hence, the on/off switch 16 of the light source 14 is engageable by the on/off switch 36 of the holder 4. The light source 14 can also include a swivelable joint 38 that enables light from the light source 14 to be directed in a direction other than parallel to the longitudinal axis of the holder 4.

In a second embodiment of the present invention, as shown in FIG. 7, the mirror assembly 20 includes a magnet 40 located on the end of the telescoping wand 22 opposite the mirror 24 and the holder 4 includes a piece of magnetic material 42, such as steel, positioned at the base of the second aperture 12. The magnet 40 and the magnetic material 42 co-operate to magnetically secure the telescoping wand 22 in the second aperture 12. If removed from the holder 4, the mirror assembly 20 can also be utilized as a telescoping magnetic pick-up tool.

Figure 8:
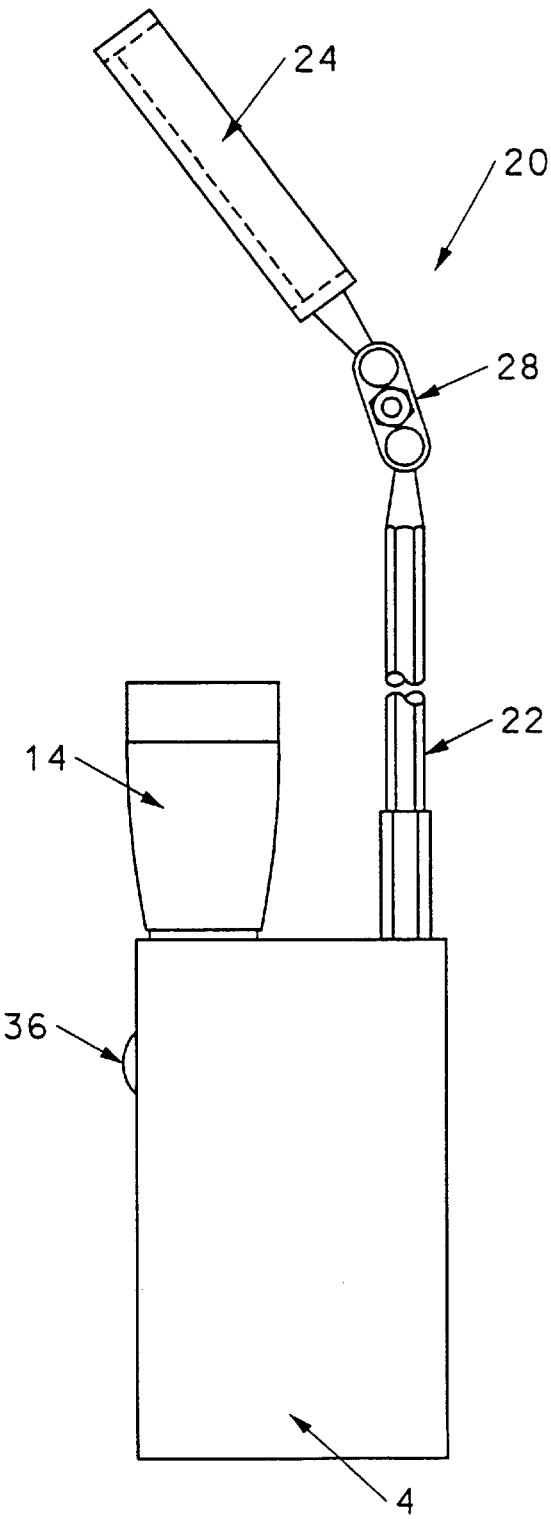
FIG. 8 is a side view of a third embodiment of an illuminated mirror tool of the present invention showing a light source and a mirror assembly integrally formed with a holder.

In a third embodiment of the present invention, as shown in FIG. 8, the light source 14 and mirror assembly 20 can be formed as an integral part of the holder 4.

In a fourth embodiment of the present invention, as shown in FIG. 9, the compressible material 18 in the first aperture 6 and the second aperture 12 can be replaced by the plurality of resilient projections 19. The projections 19 are adapted to provide frictional interaction between the light source 14 and the inner wall of the first aperture 6 and between the wand 22 of the mirror assembly 20 and the inner wall of the second aperture 12. The projections 19 can be made from rubber, neoprene or any other similar material capable of providing the required frictional interaction.

A belt carrier 44 as shown in FIGS. 10 and 11 can be utilized to transport the illuminated mirror tool. The belt carrier 44 is U-shaped and adapted to receive a waist belt of a user thereby enabling hands-free transportation and storage of the illuminated mirror tool 2 by the user.

Based on the foregoing, it can be seen that the present invention provides an illuminated mirror tool having a removably supported light source and a removable supported mirror. Further, it can also be seen that the present invention provides an illuminated mirror tool having an integrally formed light source and/or mirror assembly.

The invention has been described with reference to the preferred embodiments which are merely illustrative of the present invention and not restrictive thereof. Obvious modifications and alterations of the invention may be made without departing from the spirit and scope of the invention. The scope of the present invention is defined by the appended claims and equivalents thereto.

I claim:

1. An illuminated mirror tool comprising:
    a holder having a first end and a second end, the holder having a first non-adjustable aperture extending from the first end toward the second end and a second non-adjustable aperture extending from the first end toward the second end;
    a mirror assembly having a mirror connected to a wand, the second aperture adapted to receive the mirror assembly wherein the non-adjustable second aperture provides a slip fit frictional engagement for the mirror assembly for firmly and removably holding the mirror assembly in the second aperture; and
    a light source, the first aperture adapted to receive the light source, wherein the non-adjustable first aperture provides a slip fit frictional engagement for the light source for firmly and removably holding the light source in the non-adjustable first aperture, and wherein the holder positions the mirror assembly and the light source so that light from the light source is selectably receivable on the mirror of the mirror assembly.

2. The mirror tool as claimed in claim 1, further comprising a compressible material received in the first aperture, wherein the compressible material is positioned between the inner wall of the first aperture and the light source.

3. The mirror tool as claimed in claim 1, further comprising a compressible material received in the second aperture, wherein the compressible material is positioned between the inner wall of the second aperture and the wand of the mirror assembly.

4. The mirror tool as claimed in claim 1, wherein the mirror assembly includes a universal joint located between the mirror and the wand.

5. The mirror tool as claimed in claim 1, wherein the light source includes an on/off switch.

6. The mirror tool as claimed in claim 1, wherein the light source includes an on/off switch and the holder includes an on/off switch, wherein the on/off switch of the light source aligns with the on/off switch of the holder so that the on/off switch of the light source is engageable by the on/off switch of the holder.

7. The mirror tool as claimed in claim 1, wherein:
    the mirror assembly includes a magnet located at the end of the wand opposite the mirror, and
    a magnetically attractive material is located at a base of the second aperture.

8. The mirror tool as claimed in claim 1, wherein the light source includes a swivelable joint.

9. The illuminated mirror tool as claimed in claim 1, further including a means on said holder adapted to receive a waist belt of the user to provide hands-free transportation and storage of the illuminated mirror tool.

10. An illuminated mirror tool comprising:
    a holder having a first end and a second end, the holder having a first aperture extending from the first end toward the second end and the second aperture extending from the first end toward the second end;
    a mirror assembly having a mirror connected to a wand, the second aperture is adapted to receive the mirror assembly; and
    a light source, wherein the first aperture is adapted to receive the light source and the holder positions the mirror assembly and the light source so that light from the light source is selectively receivable on the mirror of the mirror assembly, wherein the light source is integrally formed as part of the holder.

11. The mirror tool as claimed in claim 10, wherein the wand of the mirror assembly is integrally formed as a part of the holder.

12. A holder forming an illuminated mirror tool, the holder having a first end and a second end, the holder having a first non-adjustable aperture extending from the first end to the second end and a second non-adjustable aperture extending from the first end towards the second end, the first non-adjustable aperture adapted to removably receive a light source therein wherein the non-adjustable first aperture provides a slip fit frictional engagement for firmly and removably holding the light source in the non-adjustable first aperture, the second aperture adapted to removably receive a wand of a mirror assembly, wherein the second non-adjustable aperture provides a slip fit frictional engagement for the wand of the mirror assembly for firmly and removably holding the wand of the mirror assembly within the second aperture, wherein the holder positions the mirror assembly and the light source so that light from the light source may be receivable on a mirror of the mirror assembly.

13. The holder as claimed in claim 12, further comprising a compressible material received in the first aperture, wherein the compressible material is adapted to provide the frictional engagement between the light source and the non-adjustable first aperture.

14. The holder as claimed in claim 12, further comprising a compressible material received in the second aperture, wherein the compressible material is adapted to provide the frictional engagement between the wand and the non-adjustable second aperture.

15. The holder as claimed in claim 12, wherein the holder is generally oval in cross section.

16. The holder as claimed in claim 12, wherein the holder includes an on/off switch which is adapted to be aligned with the on/off switch of the light source.

17. The holder as claimed in claim 12, further including a magnetically attractive material which is located at a base of the second aperture.

18. The holder as claimed in claim 12, wherein the holder is metal.

19. The holder as claimed in claim 12, further including a means on said holder adapted to receive a waist belt of the user to provide hands-free transportation and storage of the illuminated mirror tool.

20. An illuminated mirror tool comprising:
- a holder having a first aperture extending from the first end to the second end, and a second aperture extending from the first end towards the second end;
- a light source, the light source having an on/off switch, the light source having a swivelable joint enabling the light source to emit light in directions other than parallel to the longitudinal axis of the holder;
- a mirror assembly having a mirror connected to a wand, the mirror assembly having a universal joint located between the mirror and the wand the universal joint enabling the mirror to rotate around a longitudinal axis of the wand and to pivot about an axis transverse to the longitudinal axis of the wand; and
- a compressible material received in the first aperture and the second aperture, the compressible material conforming to an inner wall of each aperture, wherein:
- the holder is adapted so that the on/off switch of the light source projects through the holder, the holder positioning the light source and the mirror assembly so that light from the light source is receivable on the mirror of the mirror assembly,
- the compressible material is adapted to provide frictional interaction between the light source and the compressible material and between the compressible material and the inner wall of the first aperture so that the light source is removably secured in the first aperture; and
- the compressible material is also adapted to provide frictional interaction between the wand of the mirror assembly and the compressible material and between the compressible material and the inner wall of the second aperture so that the wand is removably secured in the second aperture.

* * * * *